United States Patent [19]

Allen et al.

[11] Patent Number: 5,491,265

[45] Date of Patent: Feb. 13, 1996

[54] PROCESS FOR PREPARING 6-CHLORO-2-HEXANONE FROM 1-METHYLCYCLOPENTANE

[75] Inventors: Diane E. Allen; Charles E. Tucker; Charles C. Hobbs; Ramakrishnan Chidambaram, all of Corpus Christi, Tex.

[73] Assignee: Hoechst Celanese Corporation, Somerville, N.J.

[21] Appl. No.: 395,266

[22] Filed: Feb. 28, 1995

[51] Int. Cl.$^6$ ..................................... C07C 45/51
[52] U.S. Cl. .................... 568/347; 568/838; 568/910
[58] Field of Search .................... 568/347, 838, 568/910

[56] References Cited

U.S. PATENT DOCUMENTS

| | | | |
|---|---|---|---|
| 2,497,349 | 2/1950 | Farkas et al. | 568/910 |
| 2,615,921 | 10/1952 | Dougherty et al. | 568/910 |
| 2,675,402 | 4/1954 | Englund | 568/347 |
| 2,691,682 | 10/1954 | Englund | 568/347 |

*Primary Examiner*—James H. Reamer
*Attorney, Agent, or Firm*—James J. Mullen; Donald R. Cassady

[57] ABSTRACT

A process for preparing 6-chloro-2-hexanone which comprises the steps of (a) oxidizing methylcyclopentane with ozone in the presence of a carboxylic acid and for a sufficient period of time to form 1-methylcyclopentanol; (b) reacting said 1-methylcyclopentanol with a suitable amount of an alkali metal hypochlorite in the presence of a carboxylic acid to form 1-methylcyclopentyl hypochlorite; and (c) heating said 1-methylcyclopentyl hypochlorite for a sufficient period of time to form 6-chloro-2-hexanone.

28 Claims, No Drawings

PROCESS FOR PREPARING 6-CHLORO-2-HEXANONE FROM 1-METHYLCYCLOPENTANE

BACKGROUND OF THE INVENTION

1. Field of the Invention

The present invention is directed to a novel process for preparing 6-chloro-2-hexanone.

6-Chloro-2-hexanone is a final intermediate in the manufacture of the vasodilator drug pentoxifyleine, commonly sold under the trademark Trental. The current manufacturing process for 6-chloro-2-hexanone is a three-step process starting from ethyl acetoacetate such as that described in *Organic Synthesis,* Collective Volume 5, Filman, H. Ed.; John Wiley, N.Y. (1932), pages 248–251 and 350–353. Atom efficiency of this process is modest (37%) since a molecule, each of ethanol and carbon dioxide, are lost per molecule of product made. Sodium bromide is formed as a by-product, making waste disposal an issue as well. Consequently, it is desirable to overcome these deficiencies and provide a more efficient, low-cost method to produce 6-chloro-2-hexanone.

2. Description of the Prior Art

The following prior art references are disclosed in accordance with the terms of 37 CFR 1.56, 1.93, and 1.97.

U.S. Pat. No. 2,497,349 discloses a process for preparing alicyclic alcohols from various hydrocarbons including methylcyclopentane.

U.S. Pat. No. 2,615,921 discloses a process for the oxidation of naphthenic hydrocarbons including methylcyclopentane.

U.S. Pat. No. 2,675,402 discloses a process for preparing tertiary cycloaliphatic hypohalites such as methylcyclopentyl hypochlorite.

U.S. Pat. No. 2,691,682 discloses a process for preparing omega-halo-ketones by rearrangement of tertiary cycloaliphatic hypohalites including the preparation of 6-chlorohexan-2-one by rearrangement of 1-methylcyclopentyl hypochlorite.

U.S. Pat. No. 3,391,190 discloses a continuous process for oxidizing lower alkanes and cycloalkanes, particularly cyclohexane, to ketones and alcohols.

U.S. Pat. No. 3,737,433 discloses certain oxoalkyldimethyl-xanthines for use in the pharmaceutical area.

U.S. Pat. No. 4,189,469 discloses pharmaceutical compositions for oral administration containing xanthine derivatives.

U.S. Pat. No. 4,260,845 discloses a zinc aluminate dehydration catalyst, suitably activated, as by heating in air, is employed to dehydrate a saturated alcohol (such as cyclohexanol) to produce an olefin.

U.S. Pat. No. 4,588,846 discloses a process for producing a cyclic alcohol (such as cyclopentanol) by catalytic hydration of a cyclic olefin (such as cyclopentene) in a liquid phase.

U.S. Pat. No. 4,661,639 discloses a process for producing a cyclic alcohol (such as cyclohexanol) by catalytic hydration of a cyclic olefin (such as cyclohexene).

U.S. Pat. No. 4,849,550 discloses a method for producing cycloalkanols by the hydration of cycloalkenes (such as methylcyclopentene) with aromatic sulfonic acids as a catalyst.

All of the above cited prior art and any other references mentioned herein are incorporated herein by reference in their entirety.

SUMMARY OF THE INVENTION

The present invention provides a novel and efficient process for preparing 6-chloro-2-hexanone which comprises the steps of (a) oxidizing methylcyclopentane with ozone in the presence of a carboxylic acid and for a sufficient period of time to form 1-methylcyclopentanol; (b) reacting said 1-methyl-cyclopentanol with a suitable amount of an alkali metal hypochlorite in the presence of a carboxylic acid to form 1-methylcyclopentyl hypochlorite; and (c) heating said 1-methylcyclopentyl hypochlorite for a sufficient period of time to form 6-chloro-2-hexanone.

DETAILED DESCRIPTION OF THE INVENTION

The present invention provides a very efficient process for preparing 6-chloro-2-hexanone (sometimes referred to as CHO) utilizing readily available and commercial starting materials and provides a process which does not produce unwanted by-products. Generally, this process for preparing 6-chloro-2-hexanone comprises the steps of (a) oxidizing methylcyclopentane with ozone in the presence of a carboxylic acid and for a sufficient period of time to form 1-methylcyclopentanol; (b) reacting said 1-methylcyclopentanol with a suitable amount of an alkali metal hypochlorite in the presence of a carboxylic acid to form 1-methylcyclopentyl hypochlorite; and (c) heating said 1-methylcyclopentyl hypochlorite for a sufficient period of time to form 6-chloro-2-hexanone.

In conjunction with step (a) above, methylcyclopentane (MCP) is a commercially available starting material. The conversion of MCP to 1-methylcyclopentanol (MCPO) is accomplished by reacting MCP with ozone ($O_3$) in the presence of a carboxylic acid and at a temperature from about 0° C. to about 50° C., preferably from 10° C. to about 30° C.

The carboxylic acid employed has the general formula $RCO_2H$ wherein R is an alkyl group, straight or branched, having from 1 to 8 carbon atoms, i.e. $C_1$–$C_8$. Carboxylic acids (CA) which have been found to be suitable, include without limitation, acetic acid, propionic acid, butyric acid, isobutyric acid, caproic acid, and mixtures thereof. The amount of carboxylic acid employed in step (a) is that which is sufficient to effect an ease with which the reaction takes place. In general, the molar ratio of MCP/CA is about 10:1 to about 1:10. The time required to convert MCP to MCPO is from about one minute to about six hours or longer.

The quantity of ozone ($O_3$) required is any amount which would facilitate the conversion of MCP to MCPO.

In conjunction with step (b) above, the MCPO is then reacted with an alkali metal hypochlorite (AMH), in the presence of a carboxylic acid to form 1-methylcyclopentyl hypochlorite (MCPH). The AMH is ether sodim hypochlorite, calcium hypochlorite, or mixtures thereof. The amount of AMH employed is from about 1:1 to about 5:1, preferably from about 1:1 to about 3:1 molar ratio, or equivalents of AMH to one mole of MCPO.

The temperature of the reaction mixture in this step (b) is from about −10° C. to about 30° C., preferably from about 0° C. to about 20° C.

The amount of carboxylic acid employed is at least that stoichiometric amount which is necessary to react with AMH to generate the reactive species "HOCl" and which has a significant effect on the yield of CHO and any impurities. In this regard, the molar ratio (or equivalents) of CA used is from about 1:1 to about 5:1, preferably from about 1:1 to about 2:1 of CA to one mole of MCPH. The carboxylic acid (CA) used in step (b) can either be the same or different from the CA employed in step (a). In any event, it is critical that such CA be used in step (b) since it has been found that the total absence thereof results in no formation of CHO.

In conjunction with step (c) above, the heating step (to convert the MCPH to CHO) is conducted at a temperature of at least 30° C., preferably from about 30° C. to about 60° C. The time required for this heating step is at least one minute, preferably from about one minute to about six hours.

As will be seen from the following examples, a combination of time, temperature concentrations, and acid (CA) provides a novel and efficient process which has heretofore not been obtainable.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

The following procedure was used to prepare five-gram samples of 1-methylcyclopentanol (MCPO) for each of the remaining examples. Into a three inlet glass flask (500 ml capacity), fitted with a thermometer, reflux condenser, stirrer, and sparging tube, there was added 50 ml of isobutyric acid and then 4.2 grams (50 mmol) of methylcyclopentane and it was dissolved therein. At this point, ozone ($O_3$) was bubbled through the mixture at room temperature (2 SCFH, about 3.0 wt. % $O_3$ in air) and stirring commenced. The reaction was complete after two hours and the reaction mixture diluted with 150 ml of ether to yield a single organic phase. This was then washed one time with 250 ml of saturated $NaHCO_3$ to yield an organic phase and an aqueous phase which were separated. The organic phase was then washed with sufficient (dilute) KOH to adjust the pH to 8 and thus form an organic phase and an aqueous phase which were separated. The aqueous phases of these washings were then combined, and then added thereto was a sufficient amount of KOH to adjust the pH to 8. The combined aqueous phases were then extracted by use of 150 ml ether (three times). These ether extractions were then combined and the resultant organic phase dried by use of $MgSO_4$. The $MgSO_4$ was removed by filtering and the resultant organic phase was concentrated and the MCPO was isolated by distilling (134°–138° C.) under atmospheric pressure. The final product was shown to be MCPO by NMR. There was a 95% conversion and a 99.4% selectivity.

EXAMPLE II–XXXVII

It has been reported in literature (U.S. Pat. No. 2,675,402) that 1-methylcyclopentyl hypochlorite rearranges to 6-chloro-2-hexanone. The best isolated yield reported for this rearrangement, in which NaOCl was generated in-situ by reacting $Cl_2$ with NaOH, was 72%. Replacing in situ generation of bleach with commercially available bleach gave 64% yield of 6-chloro-2-hexanone (isolated).

The reaction goes through an intermediate hypochlorite which rearranges to the chlorohexanone at low temperatures (30°–40° C.). It was important to understand the mechanistic details of each step of this reaction prior to setting up an experimental design. This was achieved through $^1H$ NMR experiments. Using the results from the NMR experiments, a Plackett-Burman experimental design was developed to evaluate the reaction variables summarized below:

| VARIABLES | RANGES | | |
| --- | --- | --- | --- |
| | Low | Medium | High |
| Hypochlorite (mol. eq) | 1.5 | 2.25 | 3 |
| Acetonitrile (mol. eq) | 3.8 | 5.8 | 7.7 |
| Acetic Acid (mol. eq) | 1.7 | 3.5 | 5.2 |
| Stir rate (rpm) | 200 | 300 | 400 |
| Type of hydochlorite ion | | Ca or Na | |

The indicated low values were selected because they gave the 64% yield of 6-chloro-2-hexanone mentioned above. Sodium hypochlorite, sold as a solution in water (5.25%), was used for that run. Calcium hypochlorite, unlike sodium hypochlorite, is sold as a crystalline solid so higher concentrations of the reaction mixture can be maintained. The high values were selected to determine if the yields increased with the increases in the variables. Analysis of the products from early reactions showed a major impurity. Mass spectroscopy of the major impurity indicated a dichloro compound. It was decided to determine the influence of these variables on dichloro compound formation as well. Tables 1–7 set forth the results of these Examples II–XXXVII. The equivalency of these entries in Tables 1–7 to the Examples II–XXXVII is shown below:

| Table | Entry Nos. | Example Nos. |
| --- | --- | --- |
| 1 | 1-13 | II–XIII |
| 2 | 1-4 | XIV–XVII |
| 3 | 1-6 | XVIII–XXIII |
| 4 | 1-3 | XXIV–XXVI |
| 5 | 1-3 | XXV–XXVII |
| 6 | 1-6 | XXVIII–XXXIII |
| 7 | 1-4 | XXXIV–XXXVII |

In all of the examples, bleach was maintained at 0° C. during the addition of 1-methylcyclopentanol at an addition rate of 3 ml/min and the reaction mixture stirred at room temperature for two hours. The subsequent rearrangement of the hypochlorite was conducted at 50° C. The results of the experimental design mentioned above are shown in Table 1. The responses that were evaluated were 6-chloro-2-hexanone yield, dichloro percent and conversion of 1-methylcyclopentanol. Statistical analysis was conducted using the SIMCA-P statistical package.

The strongest predictors for 6-chloro-2-hexanone yield were acetonitrile (increasing the amount of acetonitrile decreased the amount of 6-chloro-2-hexanone) and acetic acid (increasing the amount of acetic acid increased the amount of 6-chloro-2-hexanone). The strongest predictor for dichloro was acetic acid (increasing the amount of acetic acid increased the amount of the dichloro compound). Also, sodium hypochlorite gave better yields (besides being less expensive) than calcium hypochlorite.

Based on the statistical analysis, several additional experiments (Tables 2–7) were then conducted to further improve the conditions for the formation of 6-chloro-2-hexanone. The following conclusions were drawn from the experiments (based on GC yields):

Effect of Acetonitrile (Table 2): Acetonitrile was initially used as a solvent to dissolve 1-methylcyclopentanol and acetic acid. Reducing the amount of acetonitrile to a minimum without decreasing the yield would decrease the price of 6-chloro-2-hexanone. Eliminating acetonitrile from the reaction gave an 88% GC yield of 6-chloro-2-hexanone which was comparable to the runs with acetonitrile (compare entry 4 with entries 1, 2, and 3 in Table 2).

Effect of Acetic Acid (Table 3): A stoichiometric amount of acetic acid is necessary for the rearrangement since it reacts with sodium hypochlorite to generate the reactive species "HOCl" and so it has a significant effect on the yield of 6-chloro-2-hexanone and the dichloro impurity. It was therefore important to adjust the amount of acetic acid such that it maximized the 6-chloro-2-hexanone formed and minimized the dichloro impurity. Using 1.5 equivalents of acetic acid gave 86% yield [entry 2 (GC yield) in Table 3] of 6-chloro-2-hexanone while decreasing the dichloro impurity from 4 wt. % to 2 wt. % [compare entry 1 to entry 2 (GC yield) in Table 3 ]. Decreasing the amount of acetic acid to 1.25 equivalents gave 81% yield [entry 3 (GC yield) in Table 3] of 6-chloro-2-hexanone while the amount of dichloro impurity was not detectable by GC under these conditions. Decreasing the amount of acetic acid further decreased the yield of 6-chloro-2-hexanone dramatically (entries 4 and 5 in Table 3). No 6-chloro-2-hexanone was detected in the absence of an acid (entry 6 in Table 3).

Effect of Isobutyric Acid (Table 4): 1-Methylcyclopentanol which had been made by the ozonation of methylcyclopentane in isobutyric acid (Example 1 ), then distilled as an azeotrope with isobutyric acid (molar ratio of 2.6:1 1-methylcyclopentanol/isobutyric acid) was used. If the subsequent rearrangement could be carried out using the azeotrope it would eliminate an additional step of purifying the 1-methylcyclopentanol. Substituting isobutyric acid for acetic acid (partially or wholly) gave GC yields of 85–86% yield which was comparable to the 88% yield obtained by using acetic acid (compare entries 2 and 3 with entry 1 in Table 4).

Effect of Bleach (Table 5): Typically, excess bleach was used to carry out the rearrangement. Further experiments were carried out to minimize the amount of bleach. The reaction works well [88% (GC yield)] with 1.25 molar equivalents of sodium hypochlorite. Lowering the amount of bleach (along with the acetic acid) also decreases the dichloro impurity in the reaction (compare entries 2 and 3 with entry 1 in Table 5).

Effect of Temperature (Table 6): The dichloro impurity is presumed to be formed by the chlorination of 6-chloro-2-hexanone which means that, during the formation of 1-methylcyclopentyl hypochlorite at room temperature, some of it rearranges to 6-chloro-2-hexanone which in turn may get chlorinated further to the dichloro impurity. At 0° C. the yield of 6-chloro-2-hexanone essentially remained identical (86–89%-GC yields) to the 25 ° C. run. The dichloro impurity decreased and in some cases was not detectable by GC (compare entry 2 with 1, entry 4 with 3, and entry 6 with 5, all in Table 6).

Effect of Other Solvents for Extraction (Table 7): Attempts were directed towards replacing methylene chloride with an environmentally friendlier solvent. The best alternative solvent (ethyl acetate) gave an 82% GC yield (entry 2 in Table 7).

The best yield of 6-chloro-2-hexanone, with the least amount of impurities (as detected by GC), was obtained using 1.25 molar equivalents of sodium hypochlorite and 1.25 molar equivalents of acetic acid (entry 4 in Table 6). 6-Chloro-2-hexanone was isolated by distilling it from the reaction mixture. The experiments were done under two different sets of conditions.

1 ) Using 1.5 molar equivalents of sodium hypochlorite 3.8 molar equivalents of acetonitrile and 1.7 equivalents of acetic acid gave 80% isolated yield of 6-chloro-2-hexanone.

2) Using 1.4 molar equivalents of sodium hypochlorite and 1.25 equivalents of acetic acid gave 80% isolated yield of 6-chloro-2-hexanone.

TABLE 1

| ENTRY | NaOCl (Bleach) MMOL EQ | Amt. of ACN ML; MOLAR EQ. | Amt. of AcOH ML; MOLAR EQ. | STIR RATE RPM | ION TYPE | GC YIELD* CHO YIELD % | DI-CHLORO WT % | OTHER IMPURITIES WT % | CONVERSION, % |
|---|---|---|---|---|---|---|---|---|---|
| 1 | 1.5 | 20; 7.7 | 15; 5.2 | 400 | Na | 90 | 13.5 | <0.6% | 99 |
| 2 | 3 | 10; 3.8 | 15; 5.2 | 400 | Na | 74 | 12.6 | 6.4 | 98 |
| 3 | 1.5 | 10; 3.8 | 5; 1.7 | 400 | Na | 92 | 1.6 | 1.2 | 99 |
| 4 | 3 | 20; 7.7 | 15; 5.2 | 200 | Na | 87 | 8 | 2.2 | 98 |
| 5 | 1.5 | 20; 7.7 | 5; 1.7 | 200 | Na | 86 | 2.2 | 1.2 | 98 |
| 6 | 3 | 10; 3.8 | 5; 1.7 | 200 | Na | 90 | 0.8 | 1.8 | 98 |
| 7 | 2.25 | 15; 5.8 | 10; 3.5 | 300 | Na | 82 | 13.6 | 0.6 | 99 |
| 8 | 3 | 20; 7.7 | 5; 1.7 | 400 | Ca | 80 | 2.4 | 5.6 | 96 |
| 9 | 1.5 | 10; 3.8 | 5; 1.7 | 200 | Ca | 86 | 0.8 | 0.8 | 93 |
| 10 | 1.5 | 20; 7.7 | 15; 5.2 | 200 | Ca | 86 | 4.8 | 3.2 | 95 |
| 11 | 3 | 10; 3.8 | 15; 5.2 | 200 | Ca | 91 | 8.8 | 3.2 | 98 |
| 12 | 1.5 | 10; 3.8 | 15; 5.2 | 400 | Ca | 93 | 13.8 | <0.6% | 100 |
| 13 | 2.25 | 15; 5.8 | 10; 3.5 | 300 | Ca | 87 | 4.6 | <0.6% | 98 |

All reactions were run using 5 g of 1-methylcyclopentanol. The mixture of 1-methylcyclopentanol, acetonitrile and acetic acid was added to bleach (3 ml/min) which was maintained at 0° C., the resultant reaction mixture was stirred at room temperature for 2 h. extracted with methylene chloride, washed with sodium bicarbonate and dried over $Na_2SO_4$. The subsequent rearrangement was carried out at 50° C.
* The yield of 6-chloro-2-hexanone was based on its response factor. The response factor of 6-chloro-2-hexanone was used to calculate the yields of the impurities. The limit of detection 0.6%.

TABLE 2

Effect of Acetonitrile

| ENTRY | NaOCl (Bleach) MMOL EQ | Amt. of ACN ML; MOLAR EQ. | Amt. of AcOH ML; MOLAR EQ. | GC YIELD* CHO YIELD % | DICHLORO WT % | OTHER IMPURITIES WT % | CONVERSION, % |
|---|---|---|---|---|---|---|---|
| 1 | 1.5 | 20; 7.7 | 15; 5.2 | 90 | 13.5 | <0.6% | 99 |
| 2 | 1.5 | 10; 3.8 | 5; 1.7 | 92 | 1.6 | 1.2 | 99 |
| 3 | 3 | 20; 7.7 | 15; 5.2 | 87 | 6.4 | 2.2 | 98 |
| 4 | 1.5 | — | 5; 1.7 | 88 | 4 | 1 | 100 |

All reactions were run using 5 g of 1-methylcyclopentanol. The mixture of 1-methylcyclopentanol and acetic acid was added to bleach (3 ml/min) which was maintained at 0° C. The stir rate was maintained at 400 rpm. The resultant resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection is 0.6%.

TABLE 3

Effect of Acid

| ENTRY | Amt. of ACN ML; MOLAR EQ. | Amt. of AcOH ML; MOLAR EQ. | GC YIELD* CHO YIELD % | DICHLORO WT % | OTHER IMPURITIES WT % | CONVERSION % |
|---|---|---|---|---|---|---|
| 1 | — | 5; 1.7 | 88 | 4 | 1 | 100 |
| 2 | — | 4.3; 1.5 | 86 | 2.4 | <0.6% | 99 |
| 3 | — | 3.6; 1.26 | 81 | <0.6% | 2 | 98 |
| 4 | — | 3.1; 1.08 | 65 | <0.6% | 4 | 88 |
| 5 | — | 2.9; 1.01 | 42 | <0.6% | 5 | 85 |
| 6 | 10; 3.8 | 0; 0 | <0.6% | <0.6% | <0.6% | 71 |

All reactions were run using 5 g of 1-methylcyclopentanol. The mixture of 1-methylcyclopentanol and acetic acid was added to bleach (3 ml/min) which was maintained at 0° C. The stir rate was maintained at 400 rpm.. The resultant reaction mixture was stirred at room temperature for 2 h, extracted with methylene chloride, washed with sodium bicarbonate and dried over $Na_2SO_4$. The subsequent rearrangement was carried out at 50° C.
* The yield of 6-chloro-2-hexanone was based on its response factor. The response factor of 6-chloro-2-hexanone was used to calculate the yields of the impurities. The limit of detection was 0.6%.

TABLE 4

Effect of Isubutyric acid

| ENTRY | Amt. of RCOOH ML; MOLAR EQ. | GC YIELD* CHO YIELD % | DICHLORO WT % | OTHER IMPURITIES WT % | CONVERSION % |
|---|---|---|---|---|---|
| 1 | 5; 1.7 Acetic acid | 88 | 4 | 1 | 100 |
| 2 | 7; 1.5 Isobutyric acid | 86 | 2.4 | 1.2 | 99 |
| 3 | 1.4; 0.3 Isobutyric acid 4; 1.4 Acetic acid | 85 | 5.6 | 2.8 | 100 |

All reactions were run using 5 g of 1-methylcyclopentanol. The mixture of 1-methylcyclopentanol and acetic acid and/or isobutyric acid was added to bleach (3 ml/min) which was maintained at 0° C. The stir rate was maintained at 400 rpm. The resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor of 6-chloro-2-hexanone was used to calculate the yields of the impurities. The limit of detection was 0.6%.

TABLE 5

Effect of Bleach

| ENTRY | NaOCl (Bleach) MMOL EQ | Amt. of AcOH ML; MOLAR EQ. | GC YIELD* CHO YIELD % | DICHLORO WT % | OTHER IMPURITIES WT % | CONVERSION % |
|---|---|---|---|---|---|---|
| 1 | 1.5 | 5; 1.7 | 88 | 4 | 1 | 100 |
| 2 | 1.4 | 3.6; 1.25 | 89 | <0.6% | 1.4 | 99 |
| 3 | 1.25 | 3.6; 1.25 | 88 | 2.3 | 1.3 | 99 |

All reactions were run using 5 g of 1-methylcyclopentanol. The mixture of 1-methylcyclopentanol and acetic acid was added to bleach (3 ml/min) which was maintained at 0° C. The stir rate was maintained at 400 rpm.. The resultant reaction mixture was stirred at room temperature for 2 h, extracted with methylene chloride, washed with sodium bicarbonate and dried over $Na_2SO_4$. The subsequent rearrangement was carried out at 50° C.
* The yield of 6-chloro-2-hexanone was based on its response factor. The response factor of 6-chloro-2-hexanone was used to calculate the yields of the impurities. The limit of detection was 0.6%.

TABLE 6

Effect of Temperature

| ENTRY | TEMPERATURE FOR HYPOCHLORITE FORMATION; °C. | NaOCl (Bleach) MMOL EQ | Amt. of RCOOH ML; MOLAR EQ. | GC YIELD* CHO YIELD % | DICHLORO WT % | OTHER IMPURITIES WT % | CONVERSION % |
|---|---|---|---|---|---|---|---|
| 1 | rt | 1.4 | 3.6; 1.25 Acetic acid | 89 | <0.6% | 1.4 | 99 |
| 2 | 0 | 1.4 | 3.6; 1.25 Acetic acid | 89 | <0.6% | <0.6% | 100 |
| 3 | rt | 1.25 | 3.6; 1.25 Acetic acid | 88 | 1.6 | 1 | 99 |
| 4 | 0 | 1.25 | 3.6; 1.25 Acetic acid | 89 | <0.6% | <0.6% | 100 |
| 5 | rt | 1.5 | 7; 1.5 Isobutyric acid | 86 | 2.4 | 1.2 | 99 |
| 6 | 0 | 1.5 | 7; 1.5 Isobutyric acid | 89 | 0.8 | <0.6% | 100 |

All reactions were run using 5 g of 1-methylcyclopentanol. The mixture of 1-methylcyclopentanol and acetic acid and/or isobutyric acid was added to bleach (3 ml/min) which was maintained at 0° C. The stir rate was maintained at 400 rpm. The resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor of 6-chloro-2-hexanone was used to calculate the yields of the impurities. The limit of detection was 0.6%.

TABLE 7

Effect or Oftier Extracting Solvents

| ENTRY | Amt. of RCOOH ML; MOLAR EQ. | EXTRACTING SOLVENT | GC YIELD* CHO YIELD % | DICHLORO WT % | OTHER IMPURITIES WT % | CONVERSION % |
|---|---|---|---|---|---|---|
| 1 | 5; 1.7 acetic acid | methylene chloride | 88 | 4 | 1 | 100 |
| 2 | 7; 1.5 isobutyric acid[1] | ethylacetate | 82 | 2.8 | 0.8 | 99 |
| 3 | 5; 1.5 acetic acid | methyl t-butyl ether | 71 | 4 | 4 | 98 |
| 4 | 5; 1.5 acetic acid | methyl isobutyl ketone[2] | 81 | 2.4 | <0.6% | 85 |

[1]The acid used in this case was isobutyric acid but it's effect on the yield is very comparable to acetic acid.
[2]In this case the product was extracted with methyl isobutyl ketone, heated in the methyl isobutyl ketone solution at 50° C. and submitted for analysis.
All reactions were run using 5 g of 1-methylcyclopentanol. The mixture of 1-methylcyclopentanol and the acid was added to 1.5 molar equivalents of bleach (3 ml/min) which was maintained at 0° C., the resultant reaction mixture was stirred at room temperature for 2 h, extracted with methylene chloride, washed with sodium bicarbonate and dried over $Na_2SO_4$. The subsequent rearrangement was carried out at 50° C.
*The yield of 6-chloro-2-hexanone was based on its response factor. The response factor of 6-chloro-2-hexanone was used to calculate the yields of the impurities. The limit of detection was 0.6%.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing 6-chloro-2-hexanone which comprises the steps of (a) oxidizing methylcyclopentane with ozone in the presence of a carboxylic acid and for a sufficient period of time to form 1-methylcyclopentanol; (b) reacting said 1-methylcyclopentanol with a suitable amount of an alkali metal hypochlorite in the presence of a carboxylic acid to form 1-methylcyclopentyl hypochlorite; and (c) heating said 1-methylcyclopentyl hypochlorite for a sufficient period of time to form 6-chloro-2-hexanone.

2. The process as set forth in claim 1 wherein the carboxylic acid used in steps (a) and (b) has the formula $RCO_2H$ wherein R is alkyl $C_1$–$C_8$.

3. The process as set forth in claim 2 wherein the carboxylic acid is isobutyric acid in step (a).

4. The process as set forth in claim 2 wherein the carboxylic acid is acetic acid in step (b).

5. The process as set forth in claim 1 wherein the temperature in step (a) is from about 0° C. to about 50° C.

6. The process as set forth in claim 1 wherein the temperature in step (b) is from about −10° C. to about 30° C.

7. The process as set forth in claim 1 wherein the temperature in step (c) is from about 30° C. to about 60° C.

8. The process as set forth in claim 2 wherein the alkali metal hypochlorite is selected from the group consisting of sodium hypochlorite, calcium hypochlorite, and mixtures thereof.

9. The process as set forth in claim 2 wherein the carboxylic acid is isobutyric acid in step (b).

10. The process as set forth in claim 2 wherein the carboxylic acid is a mixture of acetic acid and isobutyric acid in step (b).

11. A process for preparing 6-chloro-2-hexanone which comprises the steps of (a) oxidizing methylcyclopentane with ozone in the presence of isobutyric acid at a temperature of from about 10° C. to about 30° C. and for a sufficient period of time to form 1-methylcyclopentanol; (b) reacting said 1-methylcyclopentanol with a suitable amount of sodium hypochlorite in the presence of acetic acid and at a temperature of from about 0° C. to about 20° C. for a sufficient period of time to form 1-methylcyclopentyl hypochlorite; and (c) heating at a temperature of from about 30° C. to about 60° C., said 1-methylcyclopentyl hypochlorite, for a sufficient period of time to form 6-chloro-2-hexanone.

12. A process for preparing 6-chloro-2-hexanone which comprises the steps of (a) reacting 1-methylcyclopentanol with a suitable amount of an alkali metal hypochlorite in the presence of a carboxylic acid to form 1-methylcyclopentyl hypochlorite; and (b) heating said 1-methylcyclopentyl hypochlorite for a sufficient period of time to form 6-chloro-2-hexanone.

13. The process as set forth in claim 12, wherein the carboxylic acid used in step (a) has the formula $RCO_2H$ where R is alkyl $C_1$–$C_8$.

14. The process as set forth in claim 12 wherein the carboxylic acid is isobutyric acid in step (a).

15. The process as set forth in claim 12 wherein the carboxylic acid is acetic acid in step (a).

16. The process as set forth in claim 12 wherein the temperature in step (a) is from about −10° C. to about 50° C.

17. The process as set forth in claim 12 wherein the temperature in step (b) is from about 0° C. to about 20° C.

18. The process as set forth in claim 12 wherein the temperature in step (b) is from about 30° C. to about 60° C.

19. The process as set forth in claim 12 wherein the alkali metal hypochlorite is selected from the group consisting of sodium hypochlorite, calcium hypochlorite, and mixtures thereof.

20. The process as set forth in claim 12 wherein the carboxylic acid is isobutyric acid in step (a).

21. The process as set forth in claim 12 wherein the carboxylic acid is a mixture of acetic acid and isobutyric acid in step (a).

22. A process for preparing 6-chloro-2-hexanone which comprises the steps of (a) reacting 1-methylcyclopentanol with a suitable amount of sodium hypochlorite in the presence of acetic acid and at a temperature of from about 0° C. to about 20° C. for a sufficient period of time to form 1-methylcyclopentyl hypochlorite; and (b) heating at a temperature of from about 30° C. to about 60° C., said 1-methylcyclopentyl hypochlorite for a sufficient period of time to form 6-chloro-2-hexanone.

23. A process for preparing 1-methylcyclopentanol which comprises the step of oxidizing methylcyclopentane with ozone in the presence of a carboxylic acid and for a sufficient period of time and at a suitable temperature to form 1-methylcyclopentanol.

24. The process as set forth in claim 23 wherein the carboxylic acid used has the formula $RCO_2H$ where R is alkyl $C_1$–$C_8$.

25. The process as set forth in claim 23 wherein the carboxylic acid is isobutyric acid.

26. The process as set forth in claim 23 wherein the carboxylic acid is acetic acid.

27. The process as set forth in claim 23 wherein the temperature is from about 0° C. to about 50° C.

28. The process as set forth in claim 23 wherein the carboxylic acid is a mixture of acetic acid and isobutyric acid.

* * * * *